United States Patent
Böttcher et al.

(10) Patent No.: US 6,583,281 B2
(45) Date of Patent: Jun. 24, 2003

(54) STABILIZED N-ALKENYLLACTAM

(75) Inventors: Arnd Böttcher, Frankenthal (DE); Rolf Pinkos, Bad Dürkheim (DE); Rudolf Erich Lorenz, Ludwigshafen (DE); Hansjörg Nickel, Neustadt (DE); Jihong He, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/851,346

(22) Filed: May 9, 2001

(65) Prior Publication Data

US 2002/0002280 A1 Jan. 3, 2002

(30) Foreign Application Priority Data

May 22, 2000 (DE) .......................................... 100 24 964

(51) Int. Cl.$^7$ ............................................. C07D 223/10
(52) U.S. Cl. ...................................................... 540/485
(58) Field of Search .......................................... 540/485

(56) References Cited

U.S. PATENT DOCUMENTS 3,149,916 A 9/1964 Schachenmeier ............ 23/179

FOREIGN PATENT DOCUMENTS

| BE | 600 351 | 2/1961 |
| GB | 2 285 983 | 8/1995 |

OTHER PUBLICATIONS

Ullmann's Enc. of Ind. Chem., 6th Ed., 1999, Electronic Release Chapter 2 "Pyrolidone".
JO 1268–675–A—Abst.
96–217194/22—JP 08081397–A, Derwent Abst.
SU–734–261—Derwent Abst.
SU 737–406—Derwent Abst.

*Primary Examiner*—Bruck Kifle
(74) *Attorney, Agent, or Firm*—Keil & Weinkauf

(57) ABSTRACT

The invention provides an N-alkenyllactam having at least a 6-membered lactam ring, stabilized by phenothiazine and/or derivatives thereof, and a process for the stabilization of N-alkenyllactams.

12 Claims, No Drawings

STABILIZED N-ALKENYLLACTAM

The present invention relates to N-alkenyllactams having at least a 6-membered lactam ring, stabilized by phenothiazine and/or derivatives thereof.

N-Alkenyllactams are used inter alia for the preparation of homopolymers and copolymers for a very wide variety of applications, for example as pigment dispersants, as washing aids, as adjuvants in cosmetic and medicinal products and as auxiliary substances in textile processing and adhesives technology, and for radiation-curing surface coatings.

During processing, storage or transportation, for example, unstabilized N-alkenyllactams tend to undergo an undesirable and uncontrollable polymerization, constituting a high safety risk. To prevent this, stabilizers are generally added to N-alkenyllactams. The most widespread practice is to add N,N'-bis(1-methylpropyl)-1,4-phenylenediamine, which is marketed by BASF AG under the trade name Kerobit® BPD. In Ullmann's Encyclopedia of Industrial Chemistry, 6th edition, 1999 Electronic Release, Chapter "2-PYRROLIDONES-N-Vinyl-2-pyrrolidone", N,N'-bis(1-methylpropyl)-1,4-phenylenediamine, for example, is mentioned as a typical stabilizer for N-vinyl-2-pyrrolidone.

Belgian patent BE 600 351 discloses the stabilization of N-vinylpyrrolidone against spontaneous polymerization during storage and distillation by the addition of an aromatic compound containing at least one secondary nitrogen atom bonded to an aromatic radical and one sulfur atom bonded to a carbon atom. One of the suitable compounds mentioned is phenothiazine, which suppresses the polymerization in concentrations down to 0.1% (1000 ppm), even at elevated temperatures.

Phenothiazine and derivatives thereof are also known as constituents of polymerization stabilizers for vinyl compounds having a vinyl group bonded to a carbon atom. JP 08081397-A describes the stabilization of acrylic acid by the presence of (i) phenothiazine and (ii) at least one halide salt. Patent application GB-A 2 285 983 describes the stabilization of acrylic acid by the presence of (i) phenothiazine, (ii) a copper dithiocarbamate compound and (iii) at least one metal or one metal compound containing Cr, Mg, Ti or Co. SU 734 216 and SU 737 406 disclose phenothiazine mixed with a quinone derivative as a polymerization inhibitor for styrene or methyl methacrylate.

JO 1268-675-A describes the stabilization of vinylpyridines, for example 4-vinylpyridine, by the presence of phenothiazine and derivatives thereof.

Another problem associated with N-alkenyllactams, apart from their tendency to undergo undesirable and uncontrollable polymerization, is their tendency to discolor, especially at temperatures above room temperature. Thus, for example, initially colorless N-vinylcaprolactam, which is stabilized with the stabilizer N,N'-bis(1-methylpropyl)-1,4-phenylenediamine conventionally used in industry, assumes a yellowish to brownish coloration even when stored for only a few hours at a temperature above room temperature, the intensity of said coloration increasing significantly with increasing storage temperature.

In many cases, when processed further, N-alkenyllactams are preferably used as the pure substances in liquid form, so all N-alkenyllactams which have a melting point above room temperature generally either have to be stored and transported at a temperature above the melting point or have to be melted by a heat treatment prior to processing. Either way, the abovementioned problem of discoloration has a particularly adverse effect, especially when dealing with N-alkenyllactams which have a melting point above room temperature, i.e. those having at least a 6-membered lactam ring. Examples which may be mentioned of N-alkenyllactams important in industry are N-vinylpiperidone, melting between about 42 and 48° C., and N-vinylcaprolactam, melting between about 34 and 35° C. (cf. Beilstein's Handbook of Organic Chemistry, 3rd and 4th supplements, volume 21, part 4, Springer Verlag Berlin, Heidelberg, N.Y. 1978, pages 3174 and 3207).

It is therefore an object of the present invention to provide stabilized N-alkenyllactams having at least a 6-membered lactam ring which no longer exhibit the abovementioned disadvantages, which have a long shelf life and which exhibit only a very low tendency to discolor, even on melting or on prolonged storage at elevated temperatures. It is a further object of the present invention to find a process for the stabilization of N-alkenyllactams having at least a 6-membered lactam ring, which process yields stabilized N-alkenyllactams with the abovementioned properties. It is a further object of the present invention to find compounds capable of being used for the stabilization of N-alkenyllactams having at least a 6-membered lactam ring, the stabilized N-alkenyllactams having the abovementioned properties.

We have found that this object is achieved by the provision of an N-alkenyllactam having at least a 6-membered lactam ring, stabilized by phenothiazine and/or derivatives thereof.

The stabilizer to be used according to the invention can be either unsubstituted as the parent substance, or monosubstituted to octasubstituted as a phenothiazine derivative. It is characterized by general formula (I):

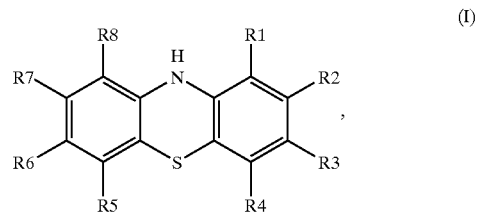

in which the radicals $R^1$ to $R^8$ independently of one another are a hydrogen atom, a carbon-containing organic radical, an amino group, a halogen, a nitro group or a cyano group.

A carbon-containing organic radical is to be understood as meaning an unsubstituted or substituted aliphatic, aromatic or araliphatic radical having from 1 to 10 carbon atoms. This radical can contain one or more heteroatoms such as oxygen, nitrogen or sulfur, for example —O—, —S—, —NR—, —CO— and/or —N= in aliphatic or aromatic systems, and/or can be substituted by one or more functional groups containing e.g. oxygen, nitrogen, sulfur and/or halogen, for example by fluorine, chlorine, bromine, iodine and/or a cyano group. If the carbon-containing organic radical contains one or more heteroatoms, said radical can also be bonded via a heteroatom. Thus ether, thioether and secondary and tertiary amino groups, for example, are also included. Preferred examples of the carbon-containing organic radical which may be mentioned are $C_1$ to $C_{10}$ alkyl, especially $C_1$ to $C_6$ alkyl, $C_6$ to $C_{10}$ aryl, especially phenyl, $C_7$ to $C_{10}$ aralkyl, especially phenylmethyl, and $C_7$ to $C_{10}$ alkaryl, especially 2-methylphenyl, 3-methylphenyl and 4-methylphenyl.

Preferred compounds of formula (I) are those in which the radicals $R^1$ to $R^8$ independently of one another are a hydrogen atom or a $C_1$ to $C_4$ alkyl, for example methyl, ethyl, propyl, 1-methylethyl, butyl, 1-methylpropyl, 2-methylpropyl and 1,1-dimethylethyl.

Particularly preferred compounds of formula (I) are those in which at least seven of the radicals $R^1$ to $R^8$ are a hydrogen atom and at most one radical is a $C_1$ to $C_4$ alkyl. Examples of particularly preferred compounds are phenothiazine, 1-methylphenothiazine, 2-methylphenothiazine, 3-methylphenothiazine and 4-methylphenothiazine. Unsubstituted phenothiazine is very particularly preferred.

The stabilizer to be employed according to the invention can be used without the addition of other stabilizers, in a mixture with one or more phenothiazine derivatives or in a mixture with other stabilizers, for example N,N'-bis(1-methylpropyl)-1,4-phenylenediamine. Use without the addition of other stabilizers is preferred.

The N-alkenyllactam stabilized according to the invention is stabilized by a total amount preferably of 1 to 1000 ppm by weight, particularly preferably of 1 to 100 ppm by weight and very particularly preferably of 5 to 50 ppm by weight of phenothiazine and/or derivatives thereof, based on the total amount of N-alkenyllactam. The expression "total amount" is always to be understood as meaning the sum of the amount of N-alkenyllactam and the amount of phenothiazine and derivatives thereof used.

In addition to phenothiazine and/or derivatives thereof, the N-alkenyllactam stabilized according to the invention can also contain other stabilizers, for example N,N'-bis(1-methylpropyl)-1,4-phenylenediamine.

The N-alkenyllactam stabilized according to the invention is characterized by at least a 6-membered lactam ring. The hydrogen atoms bonded to a carbon atom of the lactam ring can be substituted independently of one another by a carbon-containing organic radical, by an amino group, by a halogen, by a nitro group or by a cyano group. The carbon-containing organic radical is defined as previously described for formula (I).

The N-alkenyllactam stabilized according to the invention is preferably characterized by a 6- to 13-membered lactam ring and particularly preferably by a 6- to 7-membered lactam ring, examples being N-alkenylpiperidone, N-alkenylcaprolactam and derivatives thereof monosubstituted or polysubstituted by $C_1$ to $C_4$ alkyl.

The N-alkenyllactam stabilized according to the invention is further characterized by an unbranched or branched $C_2$ to $C_6$ alkenyl group with the double bond in the α-position to the lactam nitrogen, for example vinyl (ethenyl), 1-propenyl, 1-butenyl, 2-methyl-l-propenyl, 1-pentenyl or 1-hexenyl. The alkenyl group is preferably vinyl (ethenyl).

The N-alkenyllactam stabilized according to the invention is preferably N-vinylpiperidone, N-vinylcaprolactam, N-vinyl-3-methylpiperidone, N-vinyl-4-methylpiperidone, N-vinyl-5-methylpiperidone, N-vinyl-6-methylpiperidone, N-vinyl-3-ethylpiperidone, N-vinyl-4-ethylpiperidone, N-vinyl-5-ethylpiperidone, N-vinyl-6-ethylpiperidone, N-vinyl-3,5-dimethylpiperidone, N-vinyl-4,4-dimethylpiperidone, N-vinyl-3-methylcaprolactam, N-vinyl-4-methylcaprolactam, N-vinyl-5-methylcaprolactam, N-vinyl-6-methylcaprolactam, N-vinyl-7-methylcaprolactam, N-vinyl-3-ethylcaprolactam, N-vinyl-4-ethylcaprolactam, N-vinyl-5-ethylcaprolactam, N-vinyl-6-ethylcaprolactam, N-vinyl-7-ethylcaprolactam, N-vinyl-3-propylcaprolactam, N-vinyl-3-butylcaprolactam, N-vinyl-3,3-dimethylcaprolactam und N-vinyl-7,7-dimethylcaprolactam.

N-Vinylpiperidone and N-vinylcaprolactam are particularly preferred, N-vinylcaprolactam being very particularly preferred.

In addition to phenothiazine and/or derivatives thereof, the N-alkenyllactam stabilized according to the invention can also contain other stabilizers, as described above. Furthermore, the N-alkenyllactam stabilized according to the invention can also contain other N-alkenyllactams independently of their ring size, e.g. N-vinylpyrrolidone, or other components, e.g. unreacted educts or by-products from the synthesis of the N-alkenyllactam, or solvents (e.g. tetrahydrofuran or dimethylformamide). The N-alkenyllactam stabilized according to the invention preferably contains no added solvents.

Furthermore, the N-alkenyllactam stabilized according to the invention can contain dissolved gases, for example oxygen, nitrogen, carbon dioxide or inert gases like argon, or dissolved water. The dissolved substances conventionally originate from the handling of the product under the corresponding gas atmospheres. The N-alkenyllactam stabilized according to the invention preferably contains dissolved gases in the composition and amounts which arise from handling under an air atmosphere. N-Alkenyllactams stabilized in this way have a particularly low tendency to discolor.

The preferred stabilized N-alkenyllactam has an N-alkenyllactam content of >99% by weight.

A process for the stabilization of N-alkenyllactams having at least a 6-membered lactam ring has also been found wherein the N-alkenyllactam is mixed with phenothiazine and/or derivatives thereof.

In the process according to the invention, the N-alkenyllactam is mixed with a total amount preferably of 1 to 1000 ppm by weight, particularly preferably of 1 to 100 ppm by weight and very particularly preferably of 5 to 50 ppm by weight of phenothiazine and/or derivatives thereof, based on the total amount of N-alkenyllactam. The expression "total amount" is to be understood as meaning the sum of the amount of N-alkenyllactam and the amount of phenothiazine and derivatives thereof used.

The stabilization is generally effected by addition of the desired amount of phenothiazine and/or derivatives thereof to a liquid containing N-alkenyllactam, and intense mixing. As described above, in addition to the N-alkenyllactam, the liquid can also contain other components, for example by-products from the synthesis of the N-alkenyllactam, or solvents.

Phenothiazine and/or derivatives thereof can be added under various gas atmospheres, for example under an air atmosphere or under an oxygen-free and/or water vapor-free atmosphere (e.g. nitrogen or argon). Addition under air is preferred.

In principle, the stabilizer to be added according to the invention can be added as a solid, as the molten pure substance or as a solution in a suitable solvent, for example the liquid N-alkenyllactam (melted if appropriate), tetrahydrofuran or dimethylformamide. It is preferably added as a solid or dissolved in the molten N-alkenyllactam.

The origin of the N-alkenyllactam is unimportant for the process according to the invention. Thus, for example, the N-alkenyllactam can originate from the alkenylation of lactam or from other preparative processes. It is also possible to use N-alkenyllactam which has already been stabilized, either according to the invention, i.e. with phenothiazine and/or derivatives thereof, or not according to the invention, i.e. with other stabilizers.

After the stabilization according to the invention, the stabilized N-alkenyllactam can for example be worked up further, e.g. by distillation, processed for secondary products or stored in the liquid or solid state.

In the process according to the invention, the N-alkenyllactam to be stabilized and the stabilizer, i.e.

phenothiazine and/or derivatives thereof, are the compounds described earlier. The N-alkenyllactam is particularly preferably N-vinylpiperidone or N-vinylcaprolactam, especially N-vinylcaprolactam. The stabilizer is particularly preferably phenothiazine.

The use of phenothiazine and/or derivatives thereof for the stabilization of N-alkenyllactams having at least a 6-membered lactam ring, especially N-vinylcaprolactam, has also been found.

In one preferred embodiment for the stabilization of N-alkenyllactam, the desired amount of phenothiazine as a solid is added to the liquid N-alkenyllactam (previously melted if appropriate) under an air atmosphere and the components are mixed. The stabilized N-alkenyllactam can then be stored or processed further in the liquid or solid state, for example.

In another preferred embodiment, a concentrated solution of phenothiazine is prepared in said liquid N-alkenyllactam (previously melted if appropriate). The desired amount of this solution is then added to the liquid N-alkenyllactam (previously melted if appropriate) under an air atmosphere and the components are mixed. The stabilized N-alkenyllactam can then be stored or processed further in the liquid or solid state, for example.

The N-alkenyllactam stabilized according to the invention has a long shelf life and exhibits only a very low tendency to discolor, even on melting or on prolonged storage at elevated temperatures. In particular, the tendency to polymerize and discolor is considerably less pronounced than for the stabilizer N,N'-bis(1-methylpropyl)-1,4-phenylenediamine conventionally used in industry hitherto. The stabilization can advantageously be carried out under an air atmosphere.

Furthermore, even when added before or during the distillative work-up of a mixture containing N-alkenyllactam and lactam, such as that obtained e.g. in the base-catalyzed reaction of said lactam with the appropriate acetylene, the stabilizer to be used according to the invention, i.e. phenothiazine and/or derivatives thereof, has a distinct advantage over the stabilizer N,N'-bis(1-methylpropyl)-1,4-phenylenediamine conventionally used in industry hitherto, by virtue of a surprising reduction in the tendency of the lactam to polymerize. The addition of stabilizers before or during the distillative work-up is also achieved for example by the introduction of so-called stabilized bottom products. In the distillative work-up, the more volatile N-alkenyllactam is normally withdrawn at the top and the unreacted lactam is concentrated at the bottom of the column together with the higher-boiling by-products formed. Depending on the individual boiling points, said stabilizer often ends up in the bottom product. This is the case e.g. in the distillative work-up of an N-vinylcaprolactam/ε-caprolactam mixture containing phenothiazine. If N,N'-bis(1-methylpropyl)-1,4-phenylenediamine is present, the slow formation of ε-caprolactam polymers can be observed especially at the bottom of the column. Said polymers prove to be very troublesome in the distillative work-up because, for example, they can precipitate as deposits in the evaporators, prevent heat transfer and cause dangerous blockages. In the presence of phenothiazine and/or derivatives thereof, the tendency to polymerize is markedly reduced and is approximately that of the pure ε-caprolactam.

EXAMPLES

Examples 1 to 3

100 ml portions of N-vinylcaprolactam with an APHA color index of 125 (determined according to DIN ISO 6271 and DIN 6174) were melted in round-bottom flasks and optionally treated with 10 ppm by weight of each of the stabilizers mentioned. The sealed flasks were stored under an air atmosphere at 60° C. and samples were taken at regular intervals to determine the onset of polymerization, which was recognized by the appearance of turbidity in a mixture of one part of sample and nine parts of methylcyclohexane. After a storage time of 64 h, the experiment was stopped and a further sample was taken from each of the flasks to determine the APHA color index. The results are shown in Table 1.

TABLE 1

| Example | Stabilizer | Start of polymerization [h] | APHA color index after 64 h |
|---|---|---|---|
| 1* | none | 39.5 | 172 |
| 2* | 10 ppm by weight of Kerobit ® BPD | 46.0 | 186 |
| 3 | 10 ppm by weight of phenothiazine | 63.5 | 131 |

*Comparative experiment

The series of experiments shows that the N-vinylcaprolactam according to the invention, stabilized with 10 ppm by weight of phenothiazine, is significantly more stable than both the unstabilized N-vinylcaprolactam and the N-vinylcaprolactam stabilized with 10 ppm by weight of Kerobit® BPD. The start of polymerization could be delayed by time factors of about 1.6 and about 1.4 compared with the unstabilized product and the product stabilized with Kerobit® BPD, respectively.

Correspondingly, the APHA color index of the product stabilized according to the invention, i.e. 131, is by far the lowest. Compared with the APHA color index of the product originally used, i.e. 125, there has been only a very slight increase of 6. The APHA color indices of the unstabilized product and the product stabilized with Kerobit® BPD have increased markedly by 47 and 61, respectively, the greatest discoloration being exhibited by the product stabilized with Kerobit® BPD.

Examples 4 and 5

Examples 4 and 5 relate to the stabilization of a crude N-vinylcaprolactam product containing ε-caprolactam prior to distillative work-up. Because of the boiling points, N-vinylcaprolactam is withdrawn as the pure product at the top and the less volatile stabilizer is concentrated in the bottom product containing ε-caprolactam.

From the continuous distillative work-up of an unstabilized mixture carried out on the industrial scale, said mixture having been obtained by the base-catalyzed synthesis of N-vinylcaprolactam from ε-caprolactam and ethyne, the bottom product was withdrawn and analyzed. The stabilizer-free bottom product contained essentially unreacted ε-caprolactam and about 1.2% by weight of higher-boiling by-products (oligomers and polymers). 50 g portions of the bottom product were treated with 50 ppm by weight of each of the stabilizers mentioned for 11 hours under an air atmosphere at 180° C. The content of higher-boiling products was then redetermined by weighing. The results are shown in Table 2.

TABLE 2

| Example | Stabilizer | Higher-boiling by-products [% by weight] |
| --- | --- | --- |
| 4 | 50 ppm by weight of Kerobit ® BPD | 3.4 |
| 5 | 50 ppm by weight of phenothiazine | 1.3 |

Both experiments show that the use of phenothiazine also has a distinct advantage over Kerobit® BPD in suppressing the polymerization of a bottom fraction containing predominantly ε-caprolactam from the distillative work-up of crude N-vinylcaprolactam product. In example 5 according to the invention, the content of higher-boiling by-products increased by only 0.1% by weight, whereas in comparative example 4 it increased by 2.2% by weight.

We claim:

1. A composition comprising an N—$C_2$ to $C_6$ alkenylcaprolactam compound wherein the $C_2$ to $C_6$ alkenyl group is characterized by a double bond in the α-position to the lactam nitrogen and the caprolactam ring optionally may be monosubstituted or polysubstituted by $C_1$ to $C_4$ alkyl groups, stabilized by a phenothiazine compound of general formula (I)

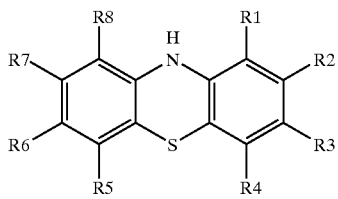

wherein the radicals $R^1$ to $R^8$ independently of one another are a hydrogen atom, an unsubstituted or substituted aliphatic, aromatic or araliphatic radical having from 1 to 10 carbon atoms, an amino group, a halogen, a nitrogen group or a cyano group, with a total amount of said phenothiazine compound of the general formula (I) of 1 to 1000 ppm by weight, based on the total amount of the N-alkenyllactam.

2. A composition comprising an N—$C_2$ to $C_6$-alkenyl-2-piperidone compound wherein the $C_2$ to $C_6$ alkenyl group is characterized by a double bond in the α-position to the lactam nitrogen and the caprolactam ring optionally may be monosubstituted or polysubstituted by $C_1$ to $C_4$ alkyl groups, stabilized by a phenothiazine compound of the general formula (I)

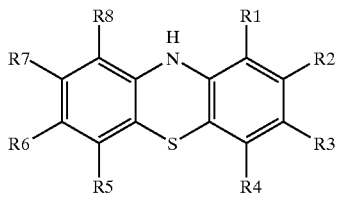

wherein the radicals $R^1$ to $R^8$ independently of one another are hydrogen atom, an unsubstituted or substituted aliphatic, aromatic or araliphatic radical having from 1 to 10 carbon atoms, an amino group, a halogen, a nitrogen group or a cyano group, with a total amount of said phenothiazine compound of the general formula (I) of 1 to 1000 ppm by weight, based on the total amount of the N-alkenyllactam.

3. An N-alkenyllaztam as claimed in claim 1, stabilized by a total amount of 1 to 100 ppm by weight of phenothiazine of the general formula (I), based on the total amount of N-alkenyllactam.

4. An N-alkenyllactam as claimed in claim 1 wherein the $C_2$- to $C_6$-alkenyl group is a vinyl group.

5. An N-alkenyllactam as claimed in claim 1 which is N-vinylcaprolactam.

6. A process for the stabilization of an N—$C_2$- to $C_6$-alkenylcaprolactam compound wherein the $C_2$ to $C_6$ alkenyl group is characterized by a double bond in the α-position to the lactam nitrogen and the caprolactam ring optionally may be monosubstituted or polysubstituted by $C_1$ to $C_4$ alkyl groups, wherein the N—$C_2$-to $C_6$-alkenylcaprolactam compound is mixed with a phenothiazine compound of the general formula (I)

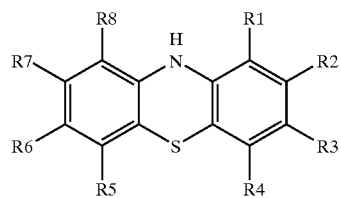

wherein the radical $R^1$ to $R^8$ independently of one another are a hydrogen atom, an unsubstituted or substituted aliphatic, aromatic or araliphatic radical having from 1 to 10 carbon atoms, an amino group, a halogen, a nitrogen group or a cyano group, with a total amount of said phenothiazine compound of the general formula (I) of 1 to 1000 ppm by weight, based on the total amount of the N-alkenyllactam.

7. A process for the stabilization of an N—$C_2$- to $C_6$-alkenyl-2-piperidone compound wherein the $C_2$ to $C_6$ alkenyl group is characterized by a double bond in the α-position to the lactam nitrogen and the caprolactam ring optionally may be monosubstituted or polysubstituted by $C_1$ to $C_4$ alkyl groups, wherein the N—$C_2$- to $C_6$-alkenylcaprolactam compound is mixed with a phenothiazine compound of the general formula (I)

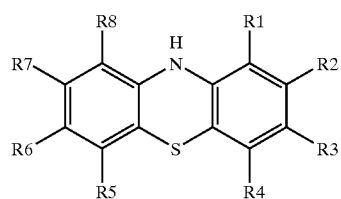

wherein the radicals $R^1$ to $R^8$ independently of one another are a hydrogen atom, an unsubstituted or substituted aliphatic, aromatic or araliphatic radical having from 1 to 10 carbon atoms, an amino group, a halogen, a nitrogen group or a cyano group, with a total amount of said phenothiazine compound of the general formula (I) of 1 to 1000 ppm by weight, based on the total amount of N-alkenyllactam.

8. A process as claimed in claim 6, wherein the N-alkenyllactam is mixed with a total amount of 1 to 100 ppm by weight of phenothiazine of the general formula (I), based on the total amount of N-alkenyllactam.

9. A process as claimed in claim 6 wherein the N-alkenyllactam is N-vinylcaprolactam.

10. An N-alkenyllactam as claimed in claim 2, stabilized by a total amount of 1 to 100 ppm by weight of phenothiazine of the general formula (I), based on the total amount of N-alkenyllactam.

11. An N-alkenyllactam as claimed in claim 2, wherein the $C_2$- to $C_6$-alkenyl group is a vinyl group.

12. A process as claimed in claim 7, wherein the N-alkenyllactam is mixed with a total amount of 1 to 100 ppm by weight of phenothiazine of the general formula (I), based on the total amount of N-alkenyllactam.

* * * * *